United States Patent [19]

Wright, Jr. et al.

[11] Patent Number: 4,542,145

[45] Date of Patent: Sep. 17, 1985

[54] SUBSTITUTED N-[(1H-1,2,4-TRIAZOL-1-YL)-ALKYL]-HETEROARYLCARBOXAMIDES

[75] Inventors: William B. Wright, Jr., Woodcliff Lake, N.J.; Jeffery B. Press, Tuxedo, N.Y.; Andrew S. Tomcufcik, Old Tappan, N.J.

[73] Assignee: American Cyanamid Company, Stamford, Conn.

[21] Appl. No.: 584,701

[22] Filed: Feb. 29, 1984

[51] Int. Cl.$^4$ .................. A61K 31/41; C07D 405/12; C07D 409/12

[52] U.S. Cl. ...................................... 514/383; 548/262

[58] Field of Search ........................ 548/262; 424/269

Primary Examiner—Alton D. Rollins
Attorney, Agent, or Firm—Mary-Ellen M. Timbers

[57] ABSTRACT

Substituted N-[(1H-1,2,4-triazol-1-yl)-alkyl]heteroarylcarboxamides are inhibitors of thromboxane synthetase enzyme.

23 Claims, No Drawings

SUBSTITUTED N-[(1H-1,2,4-TRIAZOL-1-YL)-ALKYL]-HETEROARYLCARBOXAMIDES

SUMMARY OF THE INVENTION

This invention relates to new organic compounds and, more particularly, is concerned with novel substituted N-[(1H-1,2,4-triazol-1-yl)alkyl]heteroarylcarboxamides which may be represented by the following structural formula:

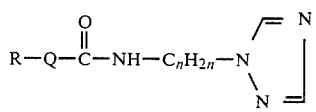

wherein n is an integer 2-5; R is a heteroaryl moiety selected from the group consisting of furanyl, mono- and disubstituted furanyl (wherein the substituents are selected from nitro and bromo), thiophene, mono- and disubstituted thiophene [wherein the substituents are selected from halogen and alkyl($C_1$-$C_3$)], benzofuran and 3-chlorobenzo[b]thiophene; and Q is

—CH=CH—, or $C_mH_{2m}$ wherein m is an integer 0-4.

The organic bases of this invention form nontoxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, maleic, fumaric and the like. For the purpose of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene and the like.

DETAILED DESCRIPTION OF THE INVENTION

The novel compounds of the present invention may be prepared according to the following flowcharts and accompanying text.

FLOWCHART A

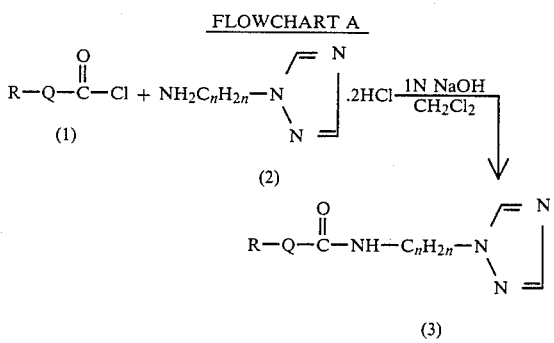

In accordance with Flowchart A, a carbonyl choride (1), where R and Q are as described above, is reacted with either 1H-1,2,4-triazole-1-alkanamine, dihydrochloride (2) or its base in a mixture of 1N sodium hydroxide and methylene chloride at room temperature (herein defined as about 15°-20° C.) for about 12-48 hours and then the organic component is concentrated, giving the product (3).

FLOWCHART B

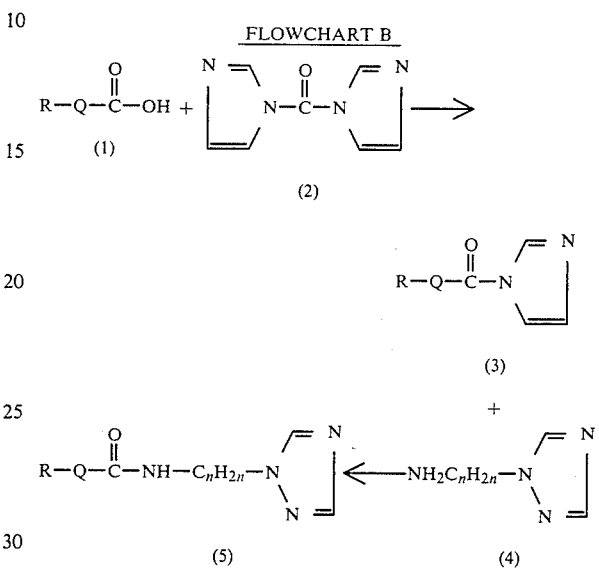

In accordance with Flowchart B, an acid (1), where R and Q are as described above, is reacted with 1,1'-carbonyldiimidazole (2) in tetrahydrofuran for about 2-4 hours, giving (3) which, without isolation, is reacted with a 1H-1,2,4-triazole-1-alkanamine (4) at reflux for about 2-4 hours giving the product (5).

The compounds of this invention inhibit thromboxane synthetase enzyme. Thus, these compounds are useful in the treatment of diseases characterized by an imbalance of thromboxane $A_2$/prostacyclin, such as ischemic heart disease, transient ischemic attack, thrombosis and migraine. Recent reviews have established the role of the thromboxane/prostacyclin balance in the vascular system [*Cardiovascular Diseases: New Trends in Surgical and Medical Aspects*, H. Barnett, P. Paoletti, E. Flamm and G. Brambilla, eds., Elsevier/North-Holland Biomedical Press, pp. 137–150 (1981)]. Prostacyclin ($PGI_2$) is a potent vasodilator and platelet aggregation inhibitor, whereas thromboxane ($TXA_2$) is a powerful vasoconstrictor and causative of platelet aggregation. $TXA_2$ is synthesized by thromboxane synthetase enzyme located in, for example, blood platelets. When $TXA_2$ production is increased relative to $PGI_2$, platelet aggregation, thrombosis and vasospasm may occur [*Lancet* (i), 1216 (1977); *Lancet*, 479 (1977); *Science*, 1135 (1976); *Amer. J. Cardiology*, 41, 787 1978)]. $TXA_2$ synthetase inhibitors have been shown to have superior anti-thrombotic action to that of aspirin [*J. Clin. Invest.*, 65, 400 (1980); *Br. J. Pharmac.*, 76, 3 (1982)].

The role of prostaglandins including $TXA_2$ and $PGI_2$ in ischemic heart patients has been reviewed [*Cardiovascular Pharmacology of the Prostaglandins*, A. G. Herman, P. M. Vanhoute, H. Denolin and A. Goosens, eds., Raven Press, New York, pp. 361-374 (1982)]. Injection of $TXA_2$ into coronary arteries of guinea pigs and rabbits causes myocardial ischemia and subendocardial necrosis [*Drugs of the Future*, 7, 331 (1982); *Proc. Jap. Acad.*, 53(B), 38 (1977); *Eur. J. Pharmacol.*, 53 49 (1978)]. Recent research has demonstrated the beneficial effects of $PGI_2$ and selective inhibition of thromboxane synthetase on ischemic myocardium in canines [*J. Cardiovascular Pharmacology*, 4 129 (1982)]. Thus compounds which selectively inhibit thromboxane synthetase (and hence $TXA_2$) without adversely affecting $PGI_2$ are useful in the treatment of vascular diseases such as ischemia and migraine. In addition, inhibition of $TXA_2$ formation may effectively treat platelet aggregation and prevent thrombosis.

Under urethan anesthesia, about 10 μl arterial blood was collected in approximately 1 ml. of about 3.2% sodium citrate in a polystyrene tube from Okamoto-Aoki spontaneously hypertensive rats (SHR) (Taconic Farms, Germantown, N.Y.) between 19 and 24 weeks in age. The blood was diluted with about 3 ml of cold saline and centrifuged at room temperature for about 15 minutes at 460 xg. The platelet rich plasma (PRP) was separated. The platelets were isolated by centrifuging the PRP for about 10 minutes at 1060 xg and were washed in about 4 ml of cold oxygenated Krebs phosphate buffer, about pH 7.4. The chilled platelets recovered from centrifuging at 800 xg for about 10 minutes were resuspended in oxygenated Krebs phosphate buffer and diluted to contain $4.5-6.0 \times 10^4$ platelets/μl.

The inhibition of thromboxane (TX) formation was studied by determining the concentration of thromboxane $B_2$ ($TXB_2$), the stable hydrolysis product of $TXA_2$. Assay samples, prepared on ice, contained about 200 μl platelet suspension, about 50 μl saline and about 50 μl vehicle or drug under study. The samples were incubated for about 10 minutes at about 37° C. in a metabolic shaker. The reaction was terminated by immersing the tubes in an ice bath and adding about 50 μl of approximately 0.5 M citric acid. The samples were centrifuged for about 10 minutes in a refrigerated centrifuge and the supernatants thus obtained were decanted and stored at about -20° C. The $TXB_2$ content for each sample was determined by a direct radioimmunoassay (RIA) utilizing a $TXB_2$ specific RIA kit purchased from New England Nuclear, Boston, Mass. and expressed as pg $TXB_2$ formed minute$^{-1}$ sample$^{-1}$, from which the percent inhibition of $TXB_2$ formation was calculated. The results of this test on representative compounds of this invention appear in Table I below.

TABLE I

| Compound | Dose | % Inhibition |
| --- | --- | --- |
| 3-chloro-N—[3-(1H—1,2,4-triazol-1-yl)propyl]benzo[b]thiophene-2-carboxamide | $10^{-4}$ | 60% |
| 5-chloro-N—[3-(1H—1,2,4-triazol-1-yl)propyl]-2-thiophenecarboxamide | $10^{-4}$ | 64% |
| N—[3-(1H—1,2,4-triazol-1-yl)propyl]-2-thiophenecarboxamide | $10^{-4}$ | 30% |
| 5-methyl-N—[3-(1H—1,2,4-triazol-1-yl)propyl]-2-thiophenecarboxamide | $10^{-4}$ | 56% |
| N—[3-(1H—1,2,4-triazol-1-yl)propyl]-3-furancarboxamide | $10^{-4}$ | 55% |
| N—[3-(1H—1,2,4-triazol-1-yl)propyl]-2-benzofurancarboxamide | $10^{-4}$ | 84% |
| 3-chloro-N—[4-(1H—1,2,4-triazol-1-yl)butyl]benzo[b]thiophene-2-carboxamide | $10^{-4}$ | 90% |
| 4,5-dibromo-N—[3-(1H—1,2,4-triazol-1-yl)propyl]-2-thiophenecarboxamide | $10^{-4}$ | 86% |
| 5-bromo-N—[3-(1H—1,2,4-triazol-1-yl)propyl]-2-furancarboxamide | $10^{-4}$ | 61% |
| N—[3-(1H—1,2,4-triazol-1-yl)propyl]-2-furancarboxamide | $10^{-4}$ | 65% |
| 5-nitro-N—[3-(1H—1,2,4-triazol-1-yl)propyl]-2-furancarboxamide | $10^{-4}$ | 70% |

TABLE I-continued

| Compound | Dose | % Inhibition |
| --- | --- | --- |
| 3-chloro-N—[2-(1H—1,2,4-triazol-1-yl)ethyl]benzo[b]thiophene-2-carboxamide | $10^{-4}$ | 90% |
| N—[3-(1H—1,2,4-triazol-1-yl)propyl]-3-(2-thienyl)-2-propanamide | $10^{-4}$ | 68% |

Hypotensive Activity in Spontaneously Hypertensive Rats

The novel compounds of the present invention are active hypotensive agents and were tested for hypotensive activity by the method of P. S. Chan and D. Poorvin, Clinical and Experimental Hypertension, 1 (6), 817-830 (1979). Male, 16 week old, spontaneously hypertensive rats of the Okamoto strain, from Taconic Farms, Germantown, N.Y., having an average mean arterial blood pressure of 170±1.5 mm of mercury are used in the test. One to 3 rats are used per test compound. A rat is dosed by gavage with a test compound, suspended in approximately 2% pre-boiled starch at a concentration of about 50 mg/ml, at a dose of about 100 mg/kg of body weight or less, with approximately 0.9% sodium chloride loading at a dose of about 25 ml/kg of body weight. A second identical dose of the test compound, without sodium chloride loading is given about 24 hours later. At about 28 hours after the initial dose the mean arterial blood pressure is measured by the method of Chan and Poorvin *vide supra*. The procedure is repeated in a second and third rat when necessary.

The results of this test on representative compounds of the present invention appear below in Table II.

TABLE II

| Compound | MABP/m Hg (No. of rats) |
| --- | --- |
| 3-chloro-N—[3-(1H—1,2,4-triazol-1-yl)propyl]benzo[b]thiophene-2-carboxamide | 137 (3) |
| 5-chloro-N—[3-(1H—1,2,4-triazol-1-yl)propyl]-2-thiophenecarboxamide | 135 (3) |
| N—[3-(1H—1,2,4-triazol-1-yl)propyl]-2-thiophenecarboxamide | 130 (3) |
| N—[3-(1H—1,2,4-triazol-1-yl)propyl]-2-benzofurancarboxamide | 135 (3) |
| 3-chloro-N—[4-(1H—1,2,4-triazol-1-yl)butyl]benzo[b]thiophene-2-carboxamide | 119 (2) |
| N—[3-(1H—1,2,4-triazol-1-yl)propyl]-2-furancarboxamide, fumarate | 116 (1) |
| 5-bromo-N—[3-(1H—1,2,4-triazol-1-yl)propyl]-2-furancarboxamide | 107 (1) |
| 5-nitro-N—[3-(1H—1,2,4-triazol-1-yl)propyl]-2-furancarboxamide | 132 (3) |
| N—[3-(1H—1,2,4-triazol-1-yl)propyl]-3-furancarboxamide | 135 (1) |
| 4,5-dibromo-N—[3-(1H—1,2,4-triazol-1-yl)propyl]-2-thiophenecarboxamide | 137 (3) |

The novel compounds of the present invention have been found to be highly useful for inhibiting thromboxane synthetase in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is about 0.25 to 0.50 mg/ml of the finished composition. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

1$\underline{H}$-1,2,4-Triazole-1-butanamine, dihydrochloride

A mixture of about 9.0 g of 1$\underline{H}$-1,2,4-triazole, about 6.24 g of approximately 50% sodium hydride in oil and about 130 ml of dimethylformamide was stirred for about 1.5 hours, then about 33 g of bromobutylphthalimide was added and this mixture was heated on a steam bath for about 6 hours, then concentrated to a solid residue. Water and methylene chloride were added, the organic layer was separated, washed with water, dried and concentrated to a residue. This residue was recrystallized from ethanol, giving about 27.3 g of 2-[4-(1$\underline{H}$-1,2,4-triazol-1-yl)butyl]-1$\underline{H}$-isoindol-1,3(2$\underline{H}$)-dione.

A mixture of about 27 g of the above dione, about 4.85 ml of hydrazine hydrate and about 250 ml of ethanol was refluxed for about 3 hours and then cooled. An approximately 450 ml portion of 3N hydrochloric acid was added and the mixture was refluxed for about 3 hours, then concentrated to about ½ volume and filtered. The filtrate was concentrated to a solid which was reconcentrated twice from ethanol, giving about 18.2 g of the desired intermediate as white crystals, mp 183°–186° C.

EXAMPLE 2

1$\underline{H}$-1,2,4-Triazole-1-ethanamine, dihydrochloride

A mixture of about 25.4 g of bromoethylphthalimide, about 10.0 g of sodium triazole and about 300 ml of dimethylformamide was heated on a steam bath for about 3 hours and then concentrated. The residue was heated twice on a steam bath with a total of about 400 ml of toluene, filtered and then cooled, giving about 10.1 g of 2-[4-(1$\underline{H}$-1,2,4-triazol-1-yl)ethyl]-1$\underline{H}$-isoindol-1,3(2$\underline{H}$)-dione.

A mixture of about 7.5 g of the above dione, about 1.70 ml of hydrazine hydrate and about 120 ml of ethanol was refluxed for about 3 hours, then cooled and about 160 ml of 3N hydrochloric acid was added. This mixture was refluxed for about 2 hours, then concentrated, water was added and the mixture filtered. The filtrate was concentrated and the residue recrystallized twice from ethanol, giving about 6.1 g of the desired intermediate as a white solid, mp 200°–210° C.

EXAMPLE 3

1H-1,2,4-Triazole-1-propanamine

A mixture of about 20.7 g of 1H-1,2,4-triazole and about 37.5 ml of acrylonitrile was heated on a steam bath for about 3 hours and then concentrated to an oil. This oil was added to about 200 ml of methanol and about 100 ml of concentrated ammonium hydroxide containing Raney nickel catalyst in a Paar apparatus and hydrogenated for about 8¼ hours with an uptake of about 46 psi of hydrogen. The catalyst was removed by filtration and ethanol was added to the filtrate. The mixture was filtered, the filtrate was concentrated, then reconcentrated from toluene, giving about 36.6 g of the desired intermediate as an oil.

EXAMPLE 4

1H-1,2,4-Triazole-1-pentanamine

A mixture of about 5.92 g of about 2.07 g of sodium triazole and about 25 ml of dimethylformamide was heated in an oil bath at about 100° C. for about 9 hours and then concentrated to remove the solvent. Methylene chloride was added and the insoluble material removed by filtration. The methylene chloride layer was washed with water, dried and concentrated. The residue was treated with ethanolic hydrochloric acid and ether and the crystalline material recovered by filtration. On recrystallization from ethanol, 2-[5-(1H-1,2,4-triazol-1-yl)pentyl]-1H-isoindol-1,3(2H)-dione, hydrochloride, mp 185°-188° C. was obtained.

A mixture of about 7.4 g of the above dione, about 2.2 g of sodium carbonate and about 10 ml of water was stirred and methylene chloride was added. The layers were separated and the organic layer dried and concentrated to remove the solvent. The residual oil, about 1.0 ml of hydrazine hydrate and about 80 ml of ethanol were refluxed for about 3 hours, cooled and about 100 ml of 3N hydochloric acid was added. This mixture was refluxed for about 2 hours, concentrated, water was added and the mixture was filtered. The filtrate was concentrated to remove volatile material and the crude dihydrochloride salt was treated with saturated potassium carbonate solution and extracted with methylene chloride. The organic layer was dried over magnesium sulfate and concentrated to obtain the desired product as an oil.

EXAMPLE 5

3-Chloro-N-[4-(1H-1,2,4-triazol-1-yl)-butyl]benzo[b]-thiophene-2-carboxamide A mixture of about 2.13 g of 1H-1,2,4-triazole-1-butanamine, dihydrochloride, about 70 ml of methylene chloride, about 30 ml of 1N sodium hydroxide and about 2.3 g of 3-chlorobenzo[b]thiophene carbonyl chloride was stirred at room temperature overnight. About five ml of 1N sodium hydroxide and about 50 ml of methylene chloride were added. The organic layer was separated, washed twice with water, dried and concentrated to an oil. The oil was crystallized from ether, giving about 2.8 g of the desired product as a yellow solid, mp 103°-105° C.

EXAMPLE 6

N-[3-(1H-1,2,4-Triazol-1-yl)propyl]-2-furancarboxamide

A mixture of about 3.78 g of 1H-1,2,4-triazole-1-propanamine, about 33 ml of 1N sodium hydroxide and about 100 ml of methylene chloride was stirred, then about 3.3 ml of 2-furoyl chloride was added. The mixture was stirred overnight, then about 15 ml of 1N sodium hydroxide and about 100 ml of methylene chloride were added. The mixture was shaken, the organic layer separated, washed with two approximately 50 ml portions of water, dried, filtered and evaporated to an oil. Ether was added to the oil which was then triturated and the crystals collected. These were recrystallized from ether giving about 2.0 g of the desired product as beige crystals, mp 63°-66° C. The fumarate salt melts at 65° C.-70° C.

Following the procedure of Example 6, but using the indicated acid chloride, the products of Example 7 and 8, found in Table III were obtained.

TABLE III

| Example | Acid Chloride | Product | MP °C. |
|---|---|---|---|
| 7 | 5-chlorothiophene carbonyl chloride | 5-chloro-N—[3-(1H—1,2,4-triazol-1-yl)propyl]-2-thiophenecarboxamide | 103–105 |
| 8 | 3-chloro-benzo[b]thiophene carbonyl chloride | 3-chloro-N—[3-(1H—1,2,4-triazol-1-yl)propyl]-benzo[b]thiophene-2-carboxamide | 101–103 |

EXAMPLE 9

5-Nitro-N-[3-(1H-1,2,4-triazol-y)propyl]-2-furancarboxamide

A mixture of about 4.71 g of 5-nitro-2-furoic acid, about 4.86 g of 1,1'-carbonyldiimidazole and about 100 ml of dry tetrahydrofuran was stirred in a 250 ml round bottom flask with a drying tube for about 3 hours. An approximately 4.0 g portion of 1H-1,2,4-triazole-1-propanamine was added and the mixture was stirred overnight at room temperature. The mixture was refluxed for about 3 hours, about 15 ml of water was added, refluxing continued for about 2 hours, then the mixture was concentrated to remove the solvents. An approximately 200 ml portion of methylene chloride and about 30 ml of 1N sodium hydroxide were added, the mixture was shaken and the organic layer separated and washed with two about 50 ml portions of water, then dried, filtered and evaporated to a solid. This solid was recrystallized from ethanol, giving about 290 mg of the desired product as beige crystals, mp 176°-177° C.

Following the procedure of Example 9, but using the indicated acids, the products of Examples 10–18, found in Table IV were obtained.

TABLE IV

| Example | Acid | Product | MP °C. |
|---|---|---|---|
| 10 | 5-bromo-2-furoic acid | 5-bromo-N—[3-(1H—1,2,4-triazol-1-yl) propyl]-2-furancarboxamide | 103–104 |
| 11 | 4,5-dibromo-2-thiophene-carboxylic acid | 4,5-dibromo-N—[3-(1H—1,2,4-triazol-1-yl)-propyl]-2-thiophene-carboxamide | 143–145 |
| 12 | coumarilic acid | N—[3-(1H—1,2,4-triazol-1-yl)propyl]-2- benzo-furancarboxamide | 113–115 |
| 13 | 3-furoic acid | N—[3-(1H—1,2,4-triazol-1-yl)propyl]-3-furan-carboxamide | 84–90 |
| 14 | 5-methyl-2-thiophenecarboxylic acid | 5-methyl-N—[3-(1H—1,2,4-triazol-1-yl)propyl]-2-thiophenecarboxamide | 96–98 |
| 15 | 2-thiophenecarboxylic acid | N—[3-(1H—1,2,4-triazol-1-yl)propyl]-2-thio- | 101–103 |

TABLE IV-continued

| Example | Acid | Product | MP °C. |
|---|---|---|---|
| 16 | 3-(2-thienyl) acrylic acid | phenecarboxamide N—[3-(1H—1,2,4-triazol-1-yl)propyl]-3-(2-thien-yl)-2-propenamide | 123–125 |
| 17 | 3-thiophene acetic acid | N—[3-(1H—1,2,4-triazol-1-yl)propyl]-3-thiophene acetamide | 50–52° |
| 18 | 2-thiophene glyoxylic acid | N—[3-(1H—1,2,4-triazol-1-yl)propyl]-α-oxo-2-thiophene acetamide | 97–99 |

EXAMPLE 19

3-Chloro-N-[2-(1H-1,2,4-triazol-1-yl)ethyl]-benzo[b]thiophene-2-carboxamide

A mixture of about 1.85 g of 1H-1,2,4-triazole-1ethanamine dihydrochloride, about 50 ml of methylene chloride, about 30 ml of 1N sodium hydroxide and about 2.3 g of 3-chlorobenzo-[b]thiophene carbonyl chloride was stirred for about 16 hours. A 50 ml portion of methylene chloride and about 5 ml of 1N sodium hydroxide were added and the layers were separated. The organic layer was washed twice with water dried and concentrated, giving the desired compound, mp 151°–152° C.

EXAMPLE 20

N-[2-(1H-1,2,4-Triazol-1-yl)ethyl]-2-furancarboxamide

Substituting 2-furoyl chloride for 3-chlorobenzo[b]thiophene carbonyl chloride in the reaction of Example 19 gave the desired compound, mp 131°–133° C.

EXAMPLE 21

N-[4-(1H-1,2,4-Triazol-1-yl)butyl]-2-furancarboxamide

A mixture of about 2.13 g of 1H-1,2,4-triazole-1-butanamine dihydrochloride, about 50 ml of methylene chloride, about 30 ml of 1N sodium hydroxide and about 1.47 ml of furoyl chloride was stirred for 16 hours and then treated with about 5 ml of 1N sodium hydroxide and about 50 ml of methylene chloride. The layers were separated and the organic layer was washed with water, dried and concentrated, giving the desired product, mp 78°–79° C.

EXAMPLE 22

5-Chloro-N-[4-(1H-1,2,4-triazol-1-yl)butyl]-2-thiophenecarboxamide

Substituting 5-chlorothiophene carbonyl chloride for furoyl chloride in the reaction of Example 21 gave the desired compound, mp 97°–99° C.

EXAMPLE 23

5-Chloro-N-[5-(1H-1,2,4-triazol-1-yl)pentyl)-2-thiophenecarboxamide

A mixture of about 1.54 g of 1H-1,2,4-triazole-1-pentanamino, about 50 ml of methylene chloride, about 10 ml of 1N sodium hydroxide and about 1.8 g of 5-chlorothiophene carboxyl chloride was stirred for about 16 hours and then treated with about 5 ml of 1N sodium hydoxide and about 50 ml of methylene chloride. The layers were separated and the organic layer was washed with water, dried and concentrated, giving the desired product, mp 79°–81° C.

What is claimed is:

1. A compound selected from those of the formula:

$$R-Q-\overset{O}{\underset{\|}{C}}-NH-C_nH_{2n}-N\underset{N}{\overset{\diagup =N}{\diagdown}}\!\!\rceil$$

wherein n is an integer 2–5; R is a heteroaryl moiety selected from the group consisting of furanyl, mono- and disubstituted furanyl (wherein the substituents are selected from nitro and bromo), thiophene, mono- and disubstituted thiophene [wherein the substituents are selected from halogen and alkyl($C_1$-$C_3$)], benzofuran and 3-chlorobenzo[b]thiophene; Q is $$-\overset{O}{\underset{\|}{C}}-,$$

—CH=CH—, or $C_mH_{2m}$ where m is an integer 0–4; and the pharmacologically acceptable acid-addition salts thereof.

2. The compound according to claim 1, 3-chloro-N-[3-(1H-1,2,4-triazol-1-yl)propyl]benzo[b]thiophene-2-carboxamide.

3. The compound according to claim 1, 5-chloro-N-[3-(1H-1,2,4-triazol-1-yl)propyl]-2-thiophenecarboxamide.

4. The compound according to claim 1, N-[3-(1H-1,2,4-triazol-1-yl)propyl]-2-thiophenecarboxamide.

5. The compound according to claim 1, 5-methyl-N-[3-(1H-1,2,4-triazol-1-yl)propyl]-2-thiophenecarboxamide.

6. The compound according to claim 1, N-[3-(1H-1,2,4-triazol-1-yl)propyl]-3-furancarboxamide.

7. The compound according to claim 1, N-[3-(1H-1,2,4-triazol-1-yl)propyl]-2-benzofurancarboxamide.

8. The compound according to claim 1, 3-chloro-N-[4-(1H-1,2,4-triazol-1-yl)butyl]benzo[b]thiophene-2-carboxamide.

9. The compound according to claim 1, 4,5-dibromo-N-[3-(1H-1,2,4-triazol-1-yl)propyl]-2-thiophenecarboxamide.

10. The compound according to claim 1, 5-bromo-N-[3-(1H-1,2,4-triazol-1-yl)-propyl]-2-furancarboxamide.

11. The compound according to claim 1, N-[3-(1H-1,2,4-triazol-1-yl)propyl]-2-furancarboxamide.

12. The compound according to claim 1, 5-nitro-N-[3-(1H-1,2,4-triazol-1-yl)propyl]-2-furancarboxamide.

13. The compound according to claim 1, N-[3-(1H-1,2,4-triazol-1-yl)propyl]-3-(2-thienyl)-2-propenamide.

14. The compound according to claim 1, N-[3-(1H-1,2,4-triazol-1-yl)propyl]-3-thiophene acetamide.

15. The compound according to claim 1, N-[3-(1H-1,2,4-triazol-1-yl)propyl]-α-oxo-2-thiophene acetamide.

16. The compound according to claim 1, 3-chloro-N-[2-(1H-1,2,4-triazol-1-yl)ethyl]benzo[b]thiophene-2-carboxamide.

17. The compound according to claim 1, N-[2-(1H-1,2,4-triazol-1-yl)ethyl]-2-furancarboxamide.

18. The compound according to claim 1, N-[4-(1H-1,2,4-triazol-1-yl)butyl]-2-furancarboxamide.

19. The compound according to claim 1, 5-chloro-N-[4-(1H-1,2,4-triazol-1-yl)butyl]-2-thiophenecarboxamide.

20. A method of inhibiting thromboxane synthetase enzyme in a mammal which comprises administering to said mammal a sufficient amount of a compound of claim 1 to effectively inhibit thromboxane synthetase enzyme in said mammal.

21. A thromboxane synthetase enzyme inhibiting composition of matter in dosage unit form comprising from about 10 mg to about 700 mg of a compound of claim 1 in association with a pharmaceutical carrier.

22. A method for inhibiting hypertension in a mammal which comprises administering to said mammal a hypotensive amount of a compound of claim 1.

23. A process for producing compounds of the formula:

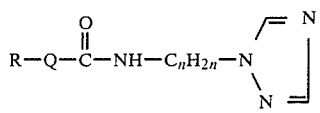

wherein n is an integer 2–5; R is a heteroaryl moiety selected from the group consisting of furanyl, mono- and disubstituted furanyl (wherein the substituents are selected from nitro and bromo), thiophene, mono and disubstituted thiophene [wherein the substituents are selected from halogen and alkyl($C_1$–$C_3$)], benzofuran and 3-chlorobenzo[b]thiophene; Q is

—CH=CH—, or $C_mH_{2m}$ where m is an integer 0–3 which comprises the steps of (a) reacting an acid of formula

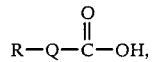

where R and Q are described above, with 1,1'-carbonylidiimidazole in tetrahydrofuran for about 2–4 hours to produce:

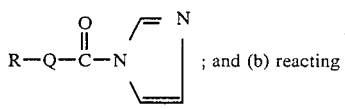 ; and (b) reacting

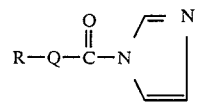

with 1H-1,2,4-triazole-1-($C_2$–$C_5$) alkanamine at reflux for about 2–4 hours.

* * * * *